United States Patent
Zhou et al.

(10) Patent No.: US 12,350,162 B2
(45) Date of Patent: Jul. 8, 2025

(54) ACETABULAR CUP AND HIP JOINT PROSTHESIS ASSEMBLY

(71) Applicant: HEFEI LONGSHORE TECH CO., LTD., Hefei (CN)

(72) Inventors: Qianlan Zhou, Hefei (CN); Lifeng Zhang, Hefei (CN); Luoping Zhou, Hefei (CN)

(73) Assignee: HEFEI LONGSHORE TECH CO., LTD, Hefei (CN)

( * ) Notice: Subject to any disclaimer, the term of this patent is extended or adjusted under 35 U.S.C. 154(b) by 0 days.

(21) Appl. No.: 18/519,992

(22) Filed: Nov. 27, 2023

(65) Prior Publication Data
US 2025/0090331 A1    Mar. 20, 2025

(30) Foreign Application Priority Data
Sep. 14, 2023  (CN) .......................... 202322503988.0

(51) Int. Cl.
*A61F 2/34*        (2006.01)
(52) U.S. Cl.
CPC ..................................... *A61F 2/34* (2013.01)
(58) Field of Classification Search
CPC .................................. A61F 2/34; A61F 2/3609
See application file for complete search history.

(56) References Cited

U.S. PATENT DOCUMENTS

| | | | | |
|---|---|---|---|---|
| 5,358,532 | A * | 10/1994 | Evans | A61F 2/34 623/22.23 |
| 7,335,231 | B2 * | 2/2008 | McLean | A61F 2/32 623/22.21 |
| 8,163,029 | B2 * | 4/2012 | Lewis | A61F 2/32 623/22.38 |
| 11,331,193 | B2 * | 5/2022 | Melozzi | A61F 2/3609 |
| 2007/0203583 | A1 * | 8/2007 | Slone | A61B 17/1666 623/22.36 |
| 2009/0005879 | A1 * | 1/2009 | Tuke | A61F 2/34 623/22.24 |
| 2017/0333192 | A1 | 11/2017 | Zhou et al. | |
| 2022/0249254 | A1 * | 8/2022 | Loiacono | A61F 2/3609 |

FOREIGN PATENT DOCUMENTS

| | | |
|---|---|---|
| CN | 201668540 U | 12/2010 |
| CN | 202821719 U | 3/2013 |
| CN | 104546227 A | 4/2015 |

(Continued)

*Primary Examiner* — Brian A Dukert
(74) *Attorney, Agent, or Firm* — BLANK ROME LLP

(57) ABSTRACT

Disclosed are an acetabular cup and a hip joint prosthesis assembly, falling within the technical field of medical instruments. The hip joint prosthesis assembly uses an acetabular cup formed by combining two layers of metal bodies, and the acetabular cup can meet the strength requirements of the cup body while ensuring that the sum of wall thicknesses of an outer cup and an inner cup is small, thereby increasing a relative rotation angle between a sphere head and the acetabular cup. The outer cup material is conducive to the fusion of the acetabular cup and the hip bone, and a spherical coronal working surface of the inner cup has high smoothness and wear-resistant hardness, which can ensure the bone ingrowth performance of the hip joint prosthesis and reduce the wear rate of the non-metallic spherical prosthesis.

8 Claims, 5 Drawing Sheets

(56) References Cited

FOREIGN PATENT DOCUMENTS

| | | |
|---|---|---|
| CN | 204411029 U | 6/2015 |
| CN | 105748174 A | 7/2016 |
| CN | 107174380 A | 9/2017 |
| CN | 109875728 A | 6/2019 |
| CN | 213346175 U | 6/2021 |
| CN | 219000733 U | 5/2023 |
| CN | 219148065 U | 6/2023 |
| CN | 221450851 U | 8/2024 |

* cited by examiner

ACETABULAR CUP AND HIP JOINT PROSTHESIS ASSEMBLY

CROSS-REFERENCE TO RELATED APPLICATIONS

This application claims priority of Chinese Patent Application No. 202322503988.0, filed on Sep. 14, 2023, the entire contents of which are incorporated herein by reference.

TECHNICAL FIELD

The present disclosure relates to the technical field of medical instruments, in particular to an acetabular cup and a hip joint prosthesis assembly.

BACKGROUND

A hip joint prosthesis generally includes a femoral handle inserted into a femur and an acetabular cup embedded in the hip bone. A sphere head connected to an upper end of the femoral handle is accommodated in the acetabular cup, and the two form a relative rotational fit. In the prior art, a nonmetallic liner is generally arranged in a metal outer cup of the acetabular cup. In order to ensure the strength of the liner, a wall body thickness of the nonmetallic liner needs to be greater than 5 mm, so that the difference between a diameter of a spherical articular surface of an inner surface of the liner matched with the sphere head and a diameter of an outer contour of the acetabular cup is large, therefore, a movement angle of the joint is small, and the sphere head is easily removed from the acetabular cup.

In order to solve the above technical problem, a nonmetallic sphere head hip joint prosthesis is disclosed in Chinese Patent CN105748174A, which eliminates the polyethylene (PE) liner inside a metal acetabular cup in the prior art, and uses the metal acetabular cup to cooperate with the nonmetallic caput femoris, so that the acetabular cup can be cooperated to the large-diameter sphere head prosthesis, thereby reducing the dislocation probability of the prosthesis. Titanium alloy is commonly used for the metal joint prosthesis. However, although titanium alloy has good biocompatibility, it is difficult to obtain a smooth surface meeting the requirements, and the wear rate between nonmetallic caput femoris and the surface is high. In addition, the acetabular cup needs to be impacted into the hip bone by knocking with a tool. When a cup wall thickness of the metal acetabular cup is small, the installment of the acetabular cup by knocking may easily lead to the deformation of the acetabular cup, which may further lead to the deformation of the spherical articular surface of the acetabular cup, resulting in poor transposition between the spherical prosthesis and the acetabular cup and aggravating the wear of the nonmetallic sphere head.

SUMMARY

An object of the present disclosure is to provide an acetabular cup and a hip joint prosthesis assembly, which can reduce the wear rate of nonmetallic spherical prostheses while increasing the range of motion of the joint.

In order to achieve the above object, the technical solutions adopted by the present disclosure are as follows.

An acetabular cup has an overall hemispherical shell shape and includes an outer cup made of titanium alloy and a metal inner cup fixedly lined in the outer cup, the strength and hardness of the inner cup being both greater than those of the outer cup, and an inner surface of the inner cup being a smooth surface.

A hip joint prosthesis assembly using the above acetabular cup includes a sphere head and a femoral handle, the sphere head being made of nonmetal. The sphere head includes a spherical component formed by cutting a part of a sphere along a plane which does not pass through a center of the sphere, an outer curved surface of the sphere head coincides with a spherical crown surface, a distance between the plane and a center of the sphere head is greater than ½ of a radius of the sphere head, and a middle part of the plane is sunken inwards to form a mounting hole for plug-fitting with the femoral handle.

Compared with the prior art, the present disclosure has the following technical effects. The hip joint prosthesis assembly uses the acetabular cup formed by combining two layers of metal bodies, the outer cup and the inner cup of the acetabular cup are made of metal materials with high strength, and the acetabular cup can meet the strength requirements of the cup body while ensuring that the sum of wall thicknesses of the outer cup and the inner cup is small, thereby increasing a relative rotation angle between the sphere head and the acetabular cup. The outer cup material is conducive to the fusion of the acetabular cup and the hip bone, and a spherical coronal working surface of the inner cup has high smoothness and wear-resistant hardness, which can ensure the bone ingrowth performance of the hip joint prosthesis and reduce the wear rate of the nonmetallic spherical prosthesis, thereby effectively improving the service life of the hip joint prosthesis assembly.

BRIEF DESCRIPTION OF THE DRAWINGS

The contents expressed in the attached drawings of the present specification and the marks in the attached drawings are briefly described as follows.

Figure 1:
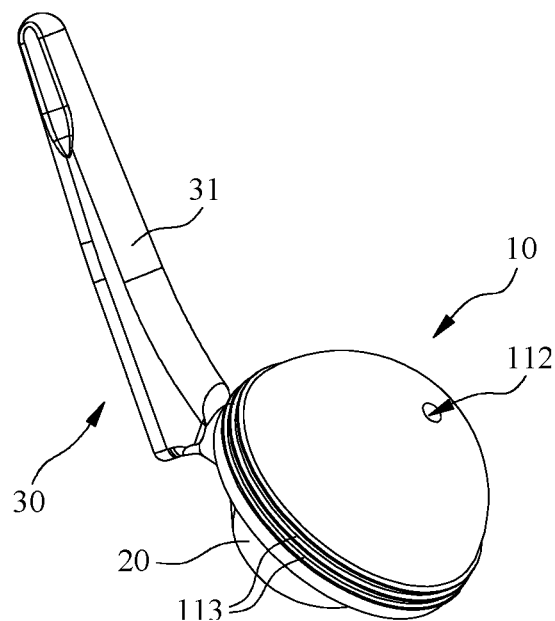
FIG. 1 is a schematic perspective view of a hip joint prosthesis assembly according to an example.

Reference numerals and denotations thereof: 10—acetabular cup; 11—outer cup; 111—flared edge; 1111—inner edge surface of the flared edge; 112—guide jack; 113—convex rib; 114—outer cup body; 12—inner cup; 121—everted edge; 122—guide protrusion; 123—inner cup body; 124—spherical crown surface; 125—everted conical surface; 13—rim end face; 20—sphere head; 21—plane; 22—mounting hole; 23—sphere head conical surface; 30—femoral handle; 31—handle body; 32—necked part; and 33—mounting base.

DETAILED DESCRIPTION

In the following, the specific implementations of the present disclosure will be further described in detail through the description of examples with reference to the attached drawings.

An acetabular cup 10 has an overall hemispherical shell shape and includes an outer cup 11 made of titanium alloy and a metal inner cup 12 fixedly lined in the outer cup 11, the strength and hardness of the inner cup 12 being both greater than those of the outer cup 11, and an inner surface of the inner cup 12 being a smooth surface. The strength of material refers to the ability of material to resist plastic deformation and fracture under the action of external force, and the hardness of material refers to the ability of material to resist harder objects being pressed into it. The metal inner cup 12 with strength and hardness greater than those of titanium alloy is lined in the outer cup 11, so that a thin-walled acetabular cup 10 can be obtained, the range of motion of the joint can be increased, and the strength of the acetabular cup body 10 can be ensured at the same time, and the working surface of the inner cup 12 can be prevented from being deformed after the acetabular cup 10 is installed. The outer cup 12 is made of titanium alloy with good biocompatibility, which can improve the fusion effect between the acetabular cup 10 and the hip bone. The inner cup 12 can be processed to obtain a spherical crown working surface with higher smoothness, and the wear rate of non-metallic spherical prosthesis can be significantly reduced by reducing a friction coefficient of the working surface.

Figure 3:
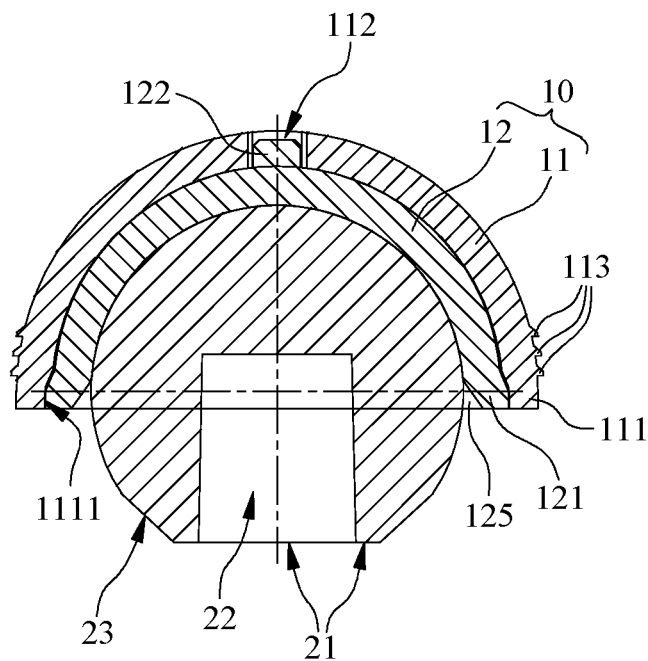
FIG. 3 is a schematic cross-sectional view of an acetabular cup and a sphere head in a fit state.
Figure 4:
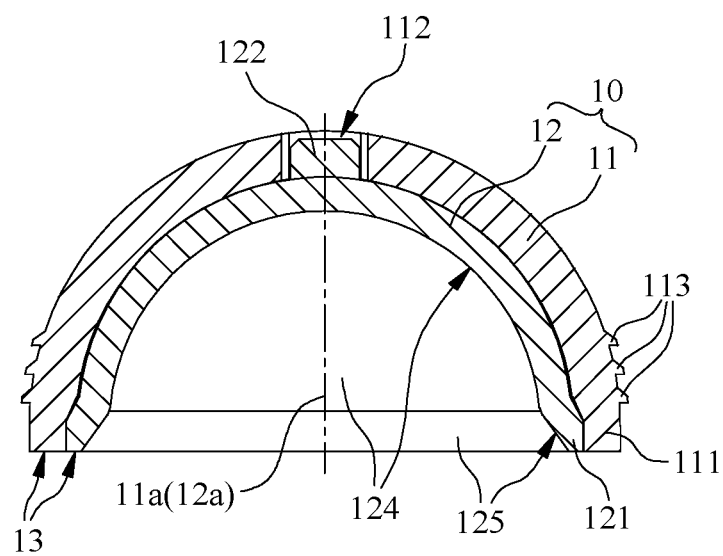
FIG. 4 is a schematic cross-sectional view of the acetabular cup.

In the example, the inner cup 12 is made of cobalt-chromium-molybdenum alloy. A cup wall thickness of the acetabular cup 10 is not greater than 5 mm, a wall thickness of the outer cup 11 being 1.2-2.5 mm and a wall thickness of the inner cup 12 being 0.8-2.5 mm. When an outer diameter of the acetabular cup 10 is smaller, as shown in FIG. 4, an outer surface area of the outer cup 11 is smaller. In order to ensure the fusion effect of the acetabular cup 10 and the hip bone, the wall thickness of the outer cup 11 is greater than that of the inner cup 12; and when the outer diameter of the acetabular cup 10 is greater, as shown in FIG. 3, the acetabular cup 10 needs to bear a large load, and the outer surface area of the outer cup 11 is greater, and the wall thickness of the inner cup 12 is greater than that of the outer cup 11 to meet the strength requirements of the acetabular cup 10.

Figure 5:
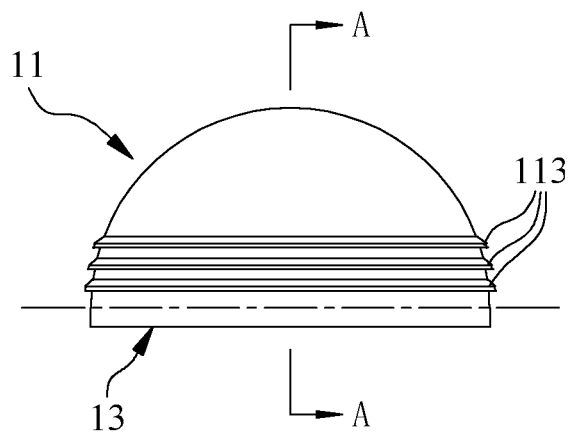
FIG. 5 is a front view of an outer cup.
Figure 6:
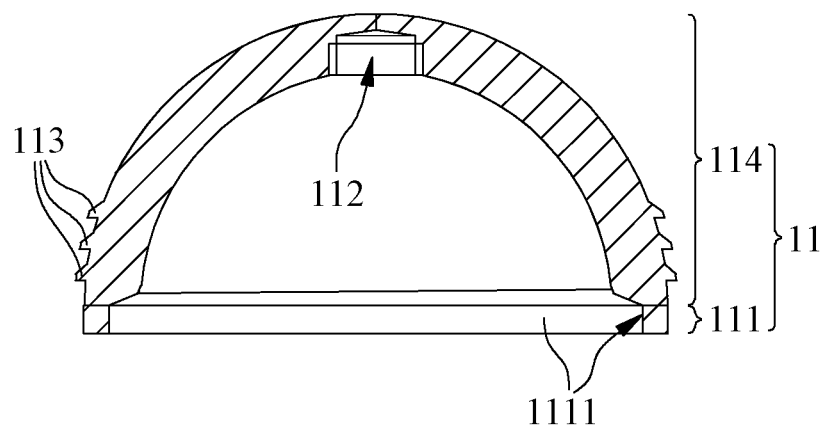
FIG. 6 is a cross-sectional view taken along a line A-A in FIG. 5.
Figure 7:
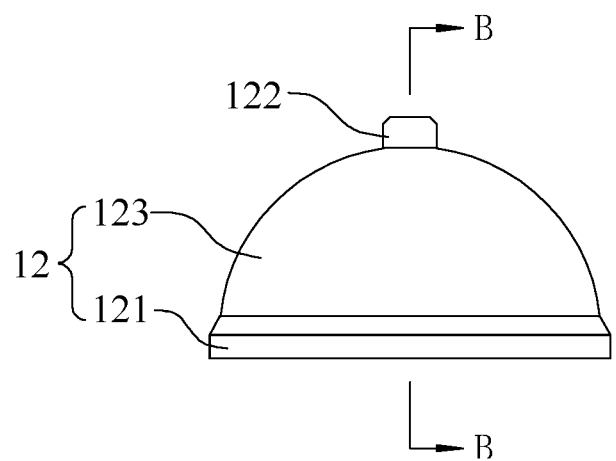
FIG. 7 is a front view of an inner cup.
Figure 8:
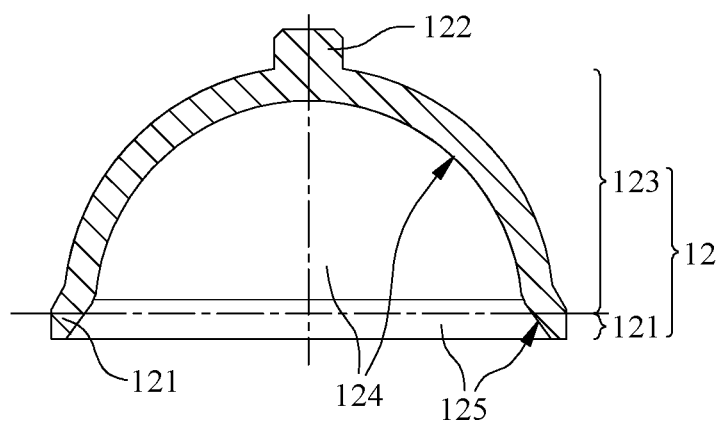
FIG. 8 is a cross-sectional view taken along a line B-B in FIG. 7.

In order to achieve a reliable connection between the outer cup 11 and the inner cup 12, in the example, the outer cup 11 is attached to a peripheral wall at a rim of the inner cup 12 to form a radial interference fit. The inner cup 12, as shown in FIGS. 7 and 8, includes an inner cup body 123, and a rim of the inner cup body 123 is connected to an everted edge 121. The outer cup 12, as shown in FIGS. 5 and 6, includes an outer cup body 114, the rim of the outer cup body 114 is connected to a thin-walled flared edge 111, and an inner edge surface of the flared edge 111 has a same shape as a periphery of the everted edge 121. When the everted edge 121 is pressed and attached to the flared edge 111, an inner surface of the inner cup body 123 is a spherical crown surface 124 forming a spherical joint fit with a sphere head 20.

During production and processing, the inner cup 12 is pressed into a cup cavity of the outer cup 11 by a tool. In order to facilitate press-mounting and positioning, a guide protrusion 122 protruding outwards is arranged on an outer wall at a crown of the inner cup 12, a guide jack 112 is correspondingly arranged at the outer cup 11, and the guide protrusion 122 and the guide jack 112 form a linear displacement fit. Meanwhile, the inner edge surface of the flared edge 111 is a cylindrical surface with a column core parallel to or coinciding with a hole core of the guide jack 112, and an axial dimension of an inner edge surface of the flared edge 1111 is less than a protruding height of the guide protrusion 122. In this way, the guide protrusion 122 is inserted into the guide jack 112, which can provide a guide for the assembly of the outer cup 11 and the inner cup 12 to ensure that the stresses on the pressed and attached surfaces of two cup bodies at the rim of the acetabular cup 10 are uniform.

An inner diameter of the inner edge surface of the flared edge 1111 is greater than that of the outer cup body 114, and the inner edge surface of the flared edge 1111 is engaged to an inner wall surface of the outer cup body 114 through an inclined surface or a curved surface. A concave cavity formed by engaging a transition inclined plane or curved surface and the inner edge surface of the flared edge 1111 accommodates the everted edge 121 of the inner cup 12.

Figure 11:
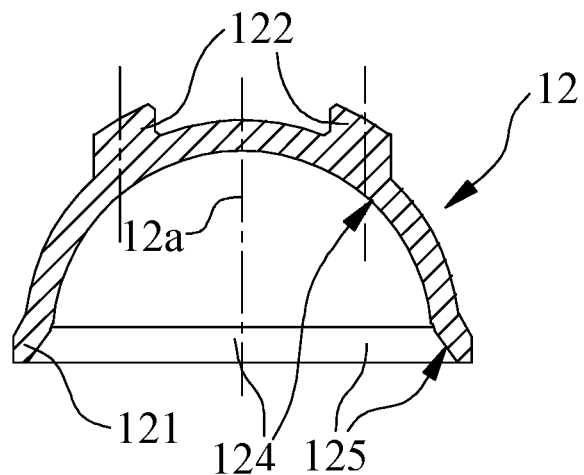
FIG. 11 is a side cross-sectional view of the inner cup.

In the examples shown in FIGS. 3, 4 and 6, the hole core of the guide jack 112 coincides with a center line 11a of the outer cup. In the solution, a shaft core of the inner edge surface of the flared edge 1111 also coincides with the hole core of the guide jack 112. In the example shown in FIG. 11, a protruding direction of the guide protrusion 122 is parallel to a center line 12a of the inner cup 12, and the shaft core of the inner edge surface of the flared edge 1111 of the outer cup 11 matched with the inner cup 12 is coincident with the center line 11a of the outer cup and parallel to the hole core of the guide jack 112 on the outer cup 11.

In the example shown in FIG. 4, a rim end face 13 of the acetabular cup 10 is perpendicular to the center line 11a of the outer cup 11, and the center line 11a of the outer cup 11 and a center line 12a of the inner cup 12 are coincident. A crown distance between the rim end face 13 and the spherical crown surface 124 is greater than a radius of the spherical crown surface 124. Preferably, the distance between the rim end face 13 and a spherical center of the spherical crown surface 124 is less than 2 mm to prevent the sphere head 20 from being removed from the acetabular cup 10, which facilitates an operator to place the sphere head 20 into the cavity of the acetabular cup 10. In order to improve the fusion performance between the acetabular cup 10 and the hip bone, an outer surface of the outer cup 11 is sprayed with a bone ingrowth material based on titanium alloy, and the outer surface of the outer cup 11 is a rough surface. In order to prevent the outer cup 11 from being removed from the hip bone at an initial stage of implantation, an outer periphery of the outer cup 11 is arranged, adjacent to the edge, with convex ribs 113 protruding outwards in a circumferential direction.

Figure 2:
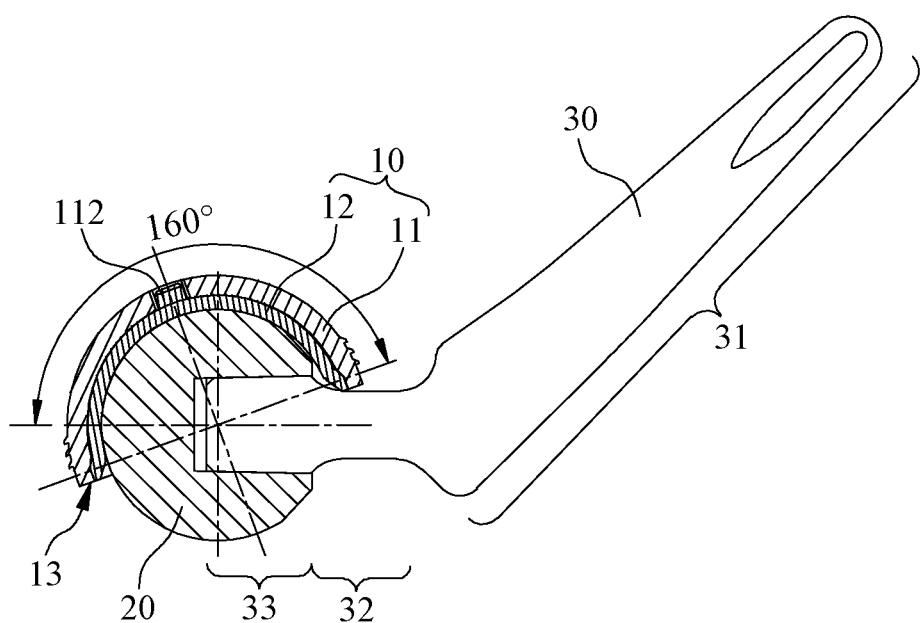
FIG. 2 is a partial sectional view of the hip joint prosthesis assembly in a fit state.
Figure 9:
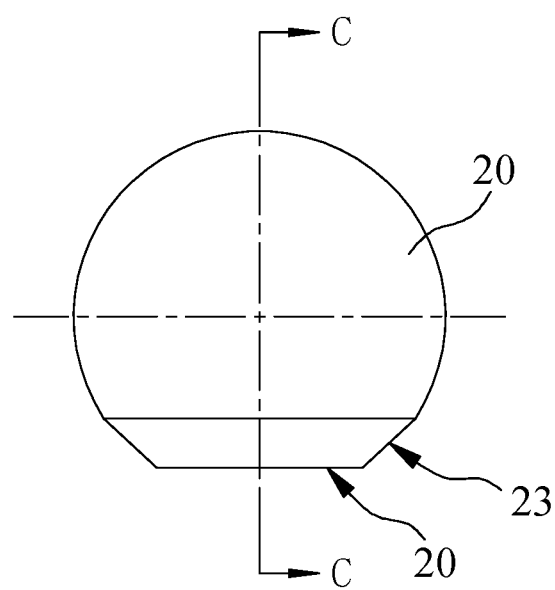
FIG. 9 is a front view of the sphere head.
Figure 10:
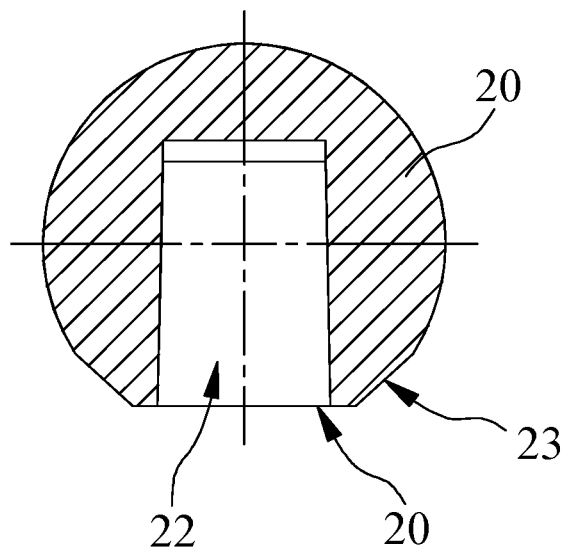
FIG. 10 is a cross-sectional view taken along a line C-C in FIG. 9.

The hip joint prosthesis assembly generally includes an acetabular cup 10, a sphere head 20 and a femoral handle 30, and the cooperation state is as shown in FIGS. 1 and 2. The sphere head 20 is made of nonmetal such as ceramic or plastic, preferably, the sphere head 20 is made of poly (ether-ether-ketone) (PEEK). The femoral handle 30 is made of metal with good biocompatibility, such as titanium alloy and cobalt-chromium-molybdenum alloy. In the example, an outer curved surface of the sphere head 20 conforms to the spherical crown surface 124. The sphere head 20 includes a spherical component formed by cutting a part of a sphere along a plane 21 which does not pass through a center of the sphere. As shown in FIGS. 9 and 10, the distance between the plane 21 and the center of the sphere head 20 is greater than ½ of the radius of the sphere head 20, so that the contact surface between the sphere head 20 and the acetabular cup 10 can be increased, thereby increasing the range of motion of the joint.

To achieve the connection of the sphere head 20 to the femoral handle 30, a middle part of the plane 21 is sunken inwards to form a mounting hole 22 for plug-fitting with the femoral handle 30. In the example, a sphere head conical surface 23 is formed around an edge of a circumferential chamfering plane 21 of the mounting hole 22, a shaft core of the sphere head conical surface 23 coincides with a hole core of the mounting hole 22, and a diameter of the sphere head conical surface 23 away from a sphere center side of the sphere head 20 is less than that of a sphere center side adjacent to the sphere head 20. Further, an end surface of the everted edge 121 of the inner cup 12 in the acetabular cup 10 is engaged to a spherical crown surface 124 through an everted conical surface 125, and the everted conical surface 125 is a conical surface with a small inside and a large outside. In this way, it is convenient for the sphere head 20 to be placed in the acetabular cup 10. In addition, when the sphere head 20 and the acetabular cup 10 are in a cooperation state, the sphere head conical surface 23 and the everted conical surface 125 can prevent adjacent tissues from being caught between the sphere head 20 and the acetabular cup 10.

The femoral handle 30 includes a handle body 31 configured to insert into a femur, an upper end of the handle body 31 is connected to a mounting base 33 of the sphere head 20 via a necked part 32, and the mounting base 33 of the sphere head 20 is inserted into the mounting hole 22 of the sphere head 20 and the two constitutes an interference fit. As shown in FIG. 2, in order to increase the rotation angle of the sphere head 20 in the acetabular cup 10, in the example, an outer diameter of the necked part 32 is less than that of the mounting base 33 of the sphere head 20, and the two is connected by a smooth curved surface in transition, so that an action angle of the hip joint prosthesis reaches 160°.

The invention claimed is:

1. An acetabular cup, the acetabular cup having an overall hemispherical shell shape, comprising an outer cup made of titanium alloy and a metal inner cup fixedly lined in the outer cup, the strength and hardness of the inner cup being both greater than those of the outer cup, and an inner surface of the inner cup being a smooth surface;
wherein the outer cup comprises an outer cup body and a rim of the outer cup, and the inner cup comprises an inner cup body and a rim of the inner cup;
wherein the rim of the inner cup is an everted edge, the rim of the outer cup is a flared edge with an inner edge surface having a same shape as a periphery of the everted edge, and the everted edge is pressed and attached to the flared edge,
wherein the inner edge surface of the flared edge is a cylindrical surface, an inner diameter of the inner edge surface of the flared edge is greater than an inner diameter of an inner wall surface of the outer cup body, and the inner edge surface of the flared edge is connected to the inner wall surface of the outer cup body through an inclined surface or a curved surface;
wherein a hip joint prosthesis assembly using the acetabular cup comprises a sphere head and a femoral handle, the sphere head being made of nonmetal, wherein a spherical component comprises the sphere head formed by cutting a part of a sphere along a plane which does not pass through a center of the sphere, an outer curved surface of the sphere head coincides with a spherical crown surface, a distance between the plane and a center of the sphere head is greater than ½ of a radius of the sphere head, and a middle part of the plane is sunken inwards to form a mounting hole for plug-fitting with the femoral handle.

2. The acetabular cup according to claim 1, wherein the outer cup is attached to a peripheral wall at the rim of the inner cup to form a radial interference fit; and an inner surface of the inner cup body is a spherical crown surface forming a spherical joint fit with the sphere head.

3. The acetabular cup according to claim 2, wherein a guide protrusion protruding outwards is arranged on an outer wall at a crown of the inner cup, a guide jack is correspondingly arranged at the outer cup, and the guide protrusion and the guide jack form a linear displacement fit;
wherein a column core of the cylindrical surface of the inner edge surface of the flared edge is parallel to or coinciding with a hole core of the guide jack.

4. The acetabular cup according to claim 3, wherein the hole core of the guide jack is parallel to or coincident with a center line of the outer cup, and a rim end face of the acetabular cup is perpendicular to the center line of the outer cup;
a crown distance between the rim end face and the spherical crown surface is greater than a radius of the spherical crown surface; and
an outer surface of the outer cup is a rough surface, and an outer periphery of the outer cup is arranged, adjacent to the edge, with convex ribs protruding outwards in a circumferential direction.

5. The acetabular cup according to claim 1, wherein the inner cup is made of cobalt-chromium-molybdenum alloy, a wall thickness of the outer cup is 1.2-2.5 mm, and a wall thickness of the inner cup is 0.8-2.5 mm.

6. A hip joint prosthesis assembly, comprising
an acetabular cup having an overall hemispherical shell shape, comprising an outer cup made of titanium alloy and a metal inner cup fixedly lined in the outer cup, the strength and hardness of the inner cup being both greater than those of the outer cup, and an inner surface of the inner cup being a smooth surface;
wherein the outer cup comprises an outer cup body and a rim of the outer cup, and the inner cup comprises an inner cup body and a rim of the inner cup;
wherein the rim of the inner cup is an everted edge, the rim of the outer cup is a flared edge with an inner edge surface having a same shape as a periphery of the everted edge, and the everted edge is pressed and attached to the flared edge,
wherein the inner edge surface of the flared edge is a cylindrical surface, an inner diameter of the inner edge surface of the flared edge is greater than an inner diameter of an inner wall surface of the outer cup body, and the inner edge surface of the flared edge is engaged connected to the inner wall surface of the outer cup body through an inclined surface or a curved surface; and
a sphere head and a femoral handle, the sphere head being made of nonmetal, wherein a spherical component comprises the sphere head formed by cutting a part of a sphere along a plane which does not pass through a center of the sphere, an outer curved surface of the sphere head coincides with a spherical crown surface, a distance between the plane and a center of the sphere head is greater than ½ of a radius of the sphere head, and a middle part of the plane is sunken inwards to form a mounting hole for plug-fitting with the femoral handle.

7. The hip joint prosthesis assembly according to claim 6, wherein the sphere head is made of poly (ether-ether-ketone) (PEEK), a sphere head conical surface is formed around an edge of a circumferential chamfering plane of the mounting hole, a shaft core of the sphere head conical surface coincides with a hole core of the mounting hole, and an end surface of the everted edge is engaged to a spherical crown surface through an everted conical surface, and the everted conical surface is a conical surface with a small inside and a large outside.

8. The hip joint prosthesis assembly according to claim 6, wherein the femoral handle comprises a handle body configured to insert into a femur, an upper end of the handle body is connected to a mounting base of the sphere head via a necked part, an outer diameter of the necked part is less than that of the mounting base of the sphere head, and the two are connected by a smooth curved surface in transition.

\* \* \* \* \*